United States Patent
Miyazaki (10) Patent No.: US 6,237,239 B1
(45) Date of Patent: *May 29, 2001

(54) HEIGHT MEASURING INSTRUMENT

(76) Inventor: Moriyuki Miyazaki, watanabe coop105 c/o nozaki higashi yaguti, 1-9-11 ota ku Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/970,416

(22) Filed: Nov. 14, 1997

(51) Int. Cl.⁷ ............................. A61B 1/100; G01B 3/10
(52) U.S. Cl. ................... 33/512; 33/755; 33/757
(58) Field of Search ................. 33/755, 757, 758, 33/759, 832, 512, 666, 677, 761, 769

(56) References Cited

U.S. PATENT DOCUMENTS

| | | | |
|---|---|---|---|
| D. 25,973 | * | 8/1896 | Schiess ........................... D10/72 |
| 564,342 | * | 7/1896 | Sherman ........................... 33/666 |
| 1,003,043 | * | 9/1911 | Goughnour ........................ 33/666 |
| 1,974,085 | * | 9/1934 | Shields et al. .................... 33/755 |
| 2,071,225 | * | 2/1937 | Buttigieg ........................... 33/769 |
| 2,197,031 | * | 11/1939 | Davis ............................... 33/755 |
| 2,325,558 | * | 7/1943 | Uslan .............................. 33/832 |
| 2,926,426 | * | 3/1960 | Lury ............................... 33/832 |
| 3,137,943 | * | 6/1964 | Mechaneck ....................... 33/833 |
| 3,144,717 | * | 8/1964 | Gumaelius ........................ 33/759 |
| 3,925,901 | * | 12/1975 | McCormick ...................... 33/759 |
| 3,994,071 | * | 11/1976 | Schoffel .......................... 33/832 |
| 4,412,384 | * | 11/1983 | Viets .............................. 33/755 |
| 5,491,907 | * | 2/1996 | Vidmar ........................... 33/832 |
| 5,996,240 | * | 12/1999 | Casper ............................ 33/512 |

FOREIGN PATENT DOCUMENTS

230727  *  4/1944  (CH)  ................................ 33/832

* cited by examiner

Primary Examiner—Jacob K. Ackun
Assistant Examiner—Faye Francis (57) ABSTRACT

A height measuring instrument includes a measuring box having a right-angled plate; a measuring tape having a scale and a space to record measured data, the measuring tape wounded onto means for winding within the measuring box when in a stored mode, being extended an optional length when in an operative mode; winding means provided within the measuring box and attached to one end portion of the measuring tape so as to wind the measuring tape by handling from the outside; means for marking the measured data on the measuring tape, the marking means being included: a measuring member formed in the shape of a plate and installed into the measuring box such that the measuring member can prevent to loosen and slide the measuring tape in an operative mode by a tension on the measuring tape when in fitting of a length of the measuring tape; a through hole formed on the measuring member and allowing writing goods to pass through therein order to record a mark on the measuring tape; a hole punch having a spring provided fixedly at the measuring member such that the hole punch mark the measured data on the measuring tape; and a step attached to another end portion of the measuring tape. Because the height measure is formed in this way, the measuring tape recorded the correct measured data of the height can be wound onto the shaft within the measuring box easily when the instrument not in measuring use, and it is a portable simply. Also, the measuring tape data can be kept as memorial goods for life.

4 Claims, 8 Drawing Sheets

HEIGHT MEASURING INSTRUMENT

BACKGROUND OF THE INVENTION

The present invention relates to a height measuring instrument that can record the measured data of the height of a user and is portable simply.

A conventional height-measuring instrument is mainly used in the hospitals, schools, gymnasiums or the like. This height measuring instrument has a right-angled plate that moves upward and downward. A user can measure a measuring value shown by the right-angled plate fitted on top of a head. An object of usage is for a medical service and social position proof.

Since the conventional height measuring instrument is too large and provided fixedly into the establishment, it can not be provided at ordinary homes. Moreover, the height measuring instrument can not be recorded the measuring value in a height measuring instrument itself, and it is just to measure an individual height.

SUMMARY OF THE INVENTION

In view of the foregoing, it is an object of the present invention to provide a height measuring instrument which can be put away while the measuring tape contains the measured data of the height of a person. It is another object of the present invention to provide a height measuring instrument which is portable easily. It is still another object of the present invention to provide a height measuring instrument which can be kept the data of child's growth through the years of growth from the date of birth and kept a history of an individual so as to check with physician's records.

DESCRIPTION OF THE PREFERRED EMBODIMENT

Preferred embodiments of the present invention are described in more detail below referring to the accompanying drawings.

An understanding of the present invention may be best gained by reference FIGS. 1 to 5. FIGS. 1 to 5 illustrate a height measuring instrument of the first embodiment of the present invention.

Figure 1:
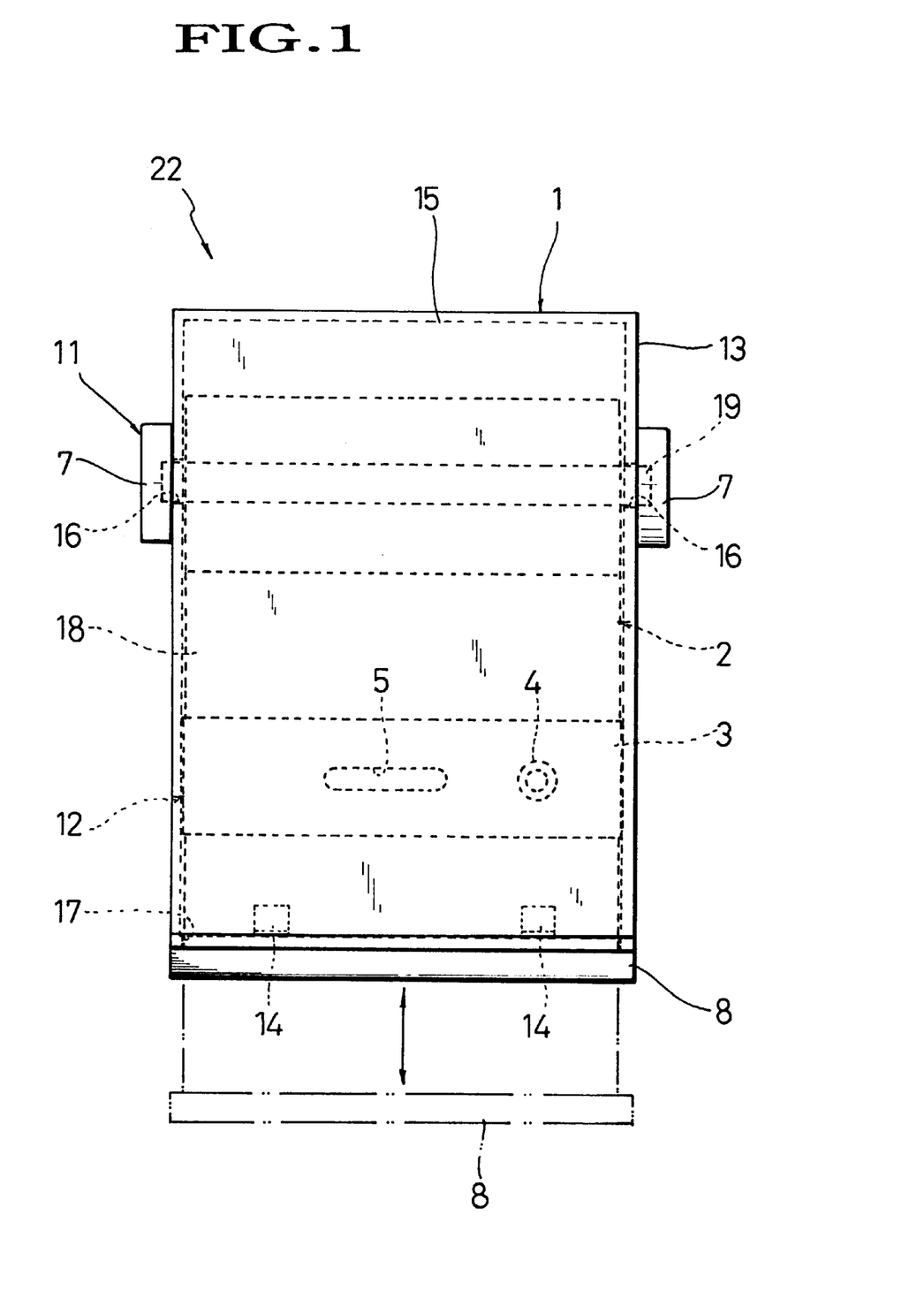
FIG. 1 is a front view showing a first embodiment of the present invention.
Figure 2:
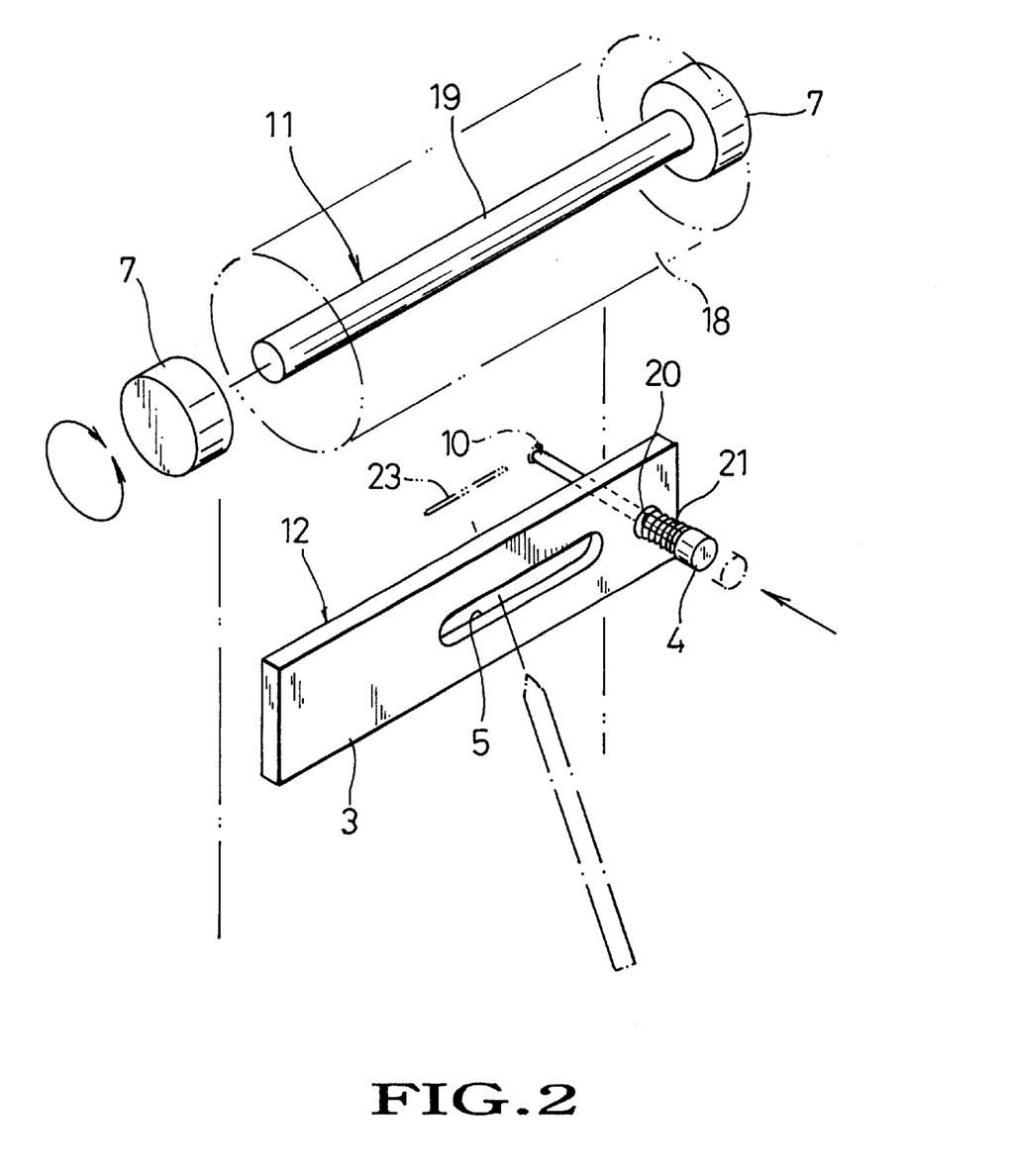
FIG. 2 is an explanatory view for a winding device of a measuring tape and a marking device showing a first embodiment of the present invention.

Numeral 22 shows a height measuring instrument of the present invention. The height measuring instrument 22 includes a measuring box 1, a measuring tape 2 having a scale 2a, being wound and stored within the measuring box 1, a measuring tape winding device 11 as means for winding the measuring tape 2 installed within the measuring box 1 such that it can wind the measuring tape 2 up within the measuring box 1, a marking device 12 as means for recording the measured data and being installed into the measuring box 1 and can mark the measured data on the measuring tape 2 during in use, and a step 8 attached to another end portion of the measuring tape 2.

The measuring box 1 includes a measuring box body 13 having an opening 1a, a right-angled plate 15, through holes 16,16 provided at an upper portions at both side faces of the measuring box body 13, and a measuring tape slot 17. The right-angled plate 15 is attached to a lower end portion of the measuring box body 13 through hinge members 14 such that the right-angled plate 15 covers the opening 1a of the measuring box body 13. The measuring tape slot 17 is located at a bottom surface of the measuring box body 13. The measuring tape slot 17 allows the measuring tape 2 to put in and out; that is, the measuring tape 2 is extended from the measuring box 1 through the measuring tape slot 17.

Figure 3:
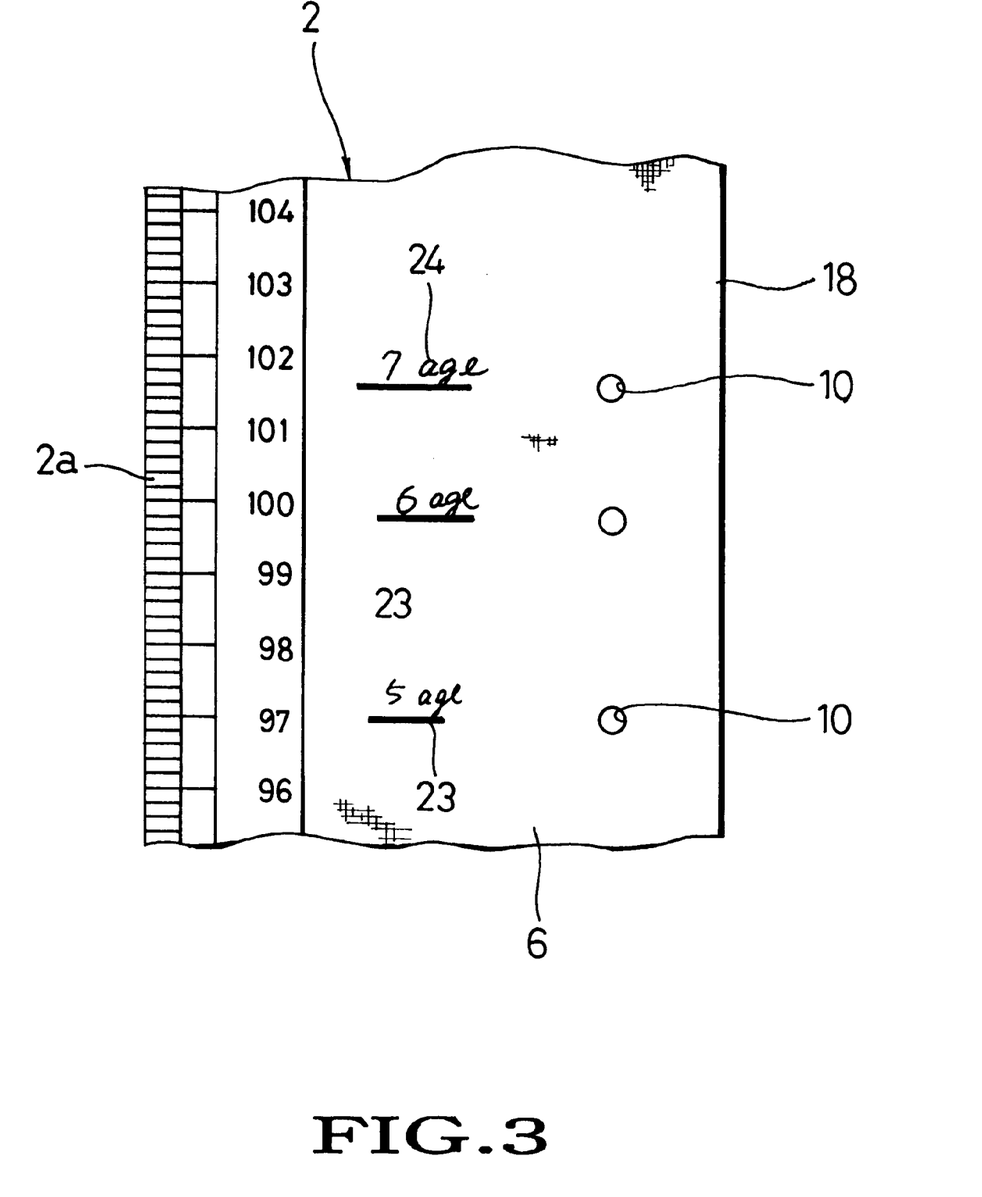
FIG. 3 is an explanatory view for a measuring tape that is recorded measured data.

The measuring tape 2 includes a measuring tape body 18, a scale 2a, and a recorded space 6. The measuring tape body 18 as bendable tape is made of synthetic resin like polyvinyl and made of a material that is able to receive marks such as letters, symbols and the like thereto by a pen and the like. The scale 2a is provided on a surface of the measuring tape body 18. The recorded space 6 is provided at a portion excepted the scale 2a at the measuring tape body 18.

The winding device 11 includes a core rod 19 and knobs 7,7. The core rod is inserted rotatably into the through holes 16,16 of the measuring box 1 such that both ends of the core rod 19 protrude outwardly. One end portion of the measuring tape 2 is attached to the core rod 19. The knobs 17,17 are provided at each of ends of the core rod 19 respectively and in operative relation to the core rod 19. Therefore, the measuring tape 2 is wound onto the core rods 17,17 within the measuring box 1 when a user rotates the knobs 17,17.

The marking device 12 includes a measuring member 3 in a shape of a plate marking hole 5 as a writing hole, a through hole 20 and a hole punch 4. The measuring member 3 is provided at a portion adjacent to a center portion of the measuring box body 13 such that it can prevent to loosen and slide the measuring tape 2 into the measuring box body 13. The measuring member 3 has a transparent body and made of synthetic resin. The elongated marking hole 5 is located substantially at a center portion of the measuring member 3, the marking hole 5 allowing a pen such as a pencil, ballpoint pen or the like to pass through therein in order to mark a line 23 as marking on the measuring tape 2. The through hole 20 is provided adjacent the marking hole 5 on the measuring member 3. The hole punch 4 having a spring 21 is provided fixedly at the measuring member 3 such that the hole punch 4 can make a punch hole 10 as a mark on the recorded space 6 of the measuring tape 2.

In the handling of the above-described apparatus, the height measuring instrument 22 of the present invention is used for providing at a corner between a vertical surface X such as a wall or pillar of a house and a horizontal surface Y such as a floor.

Figure 4:
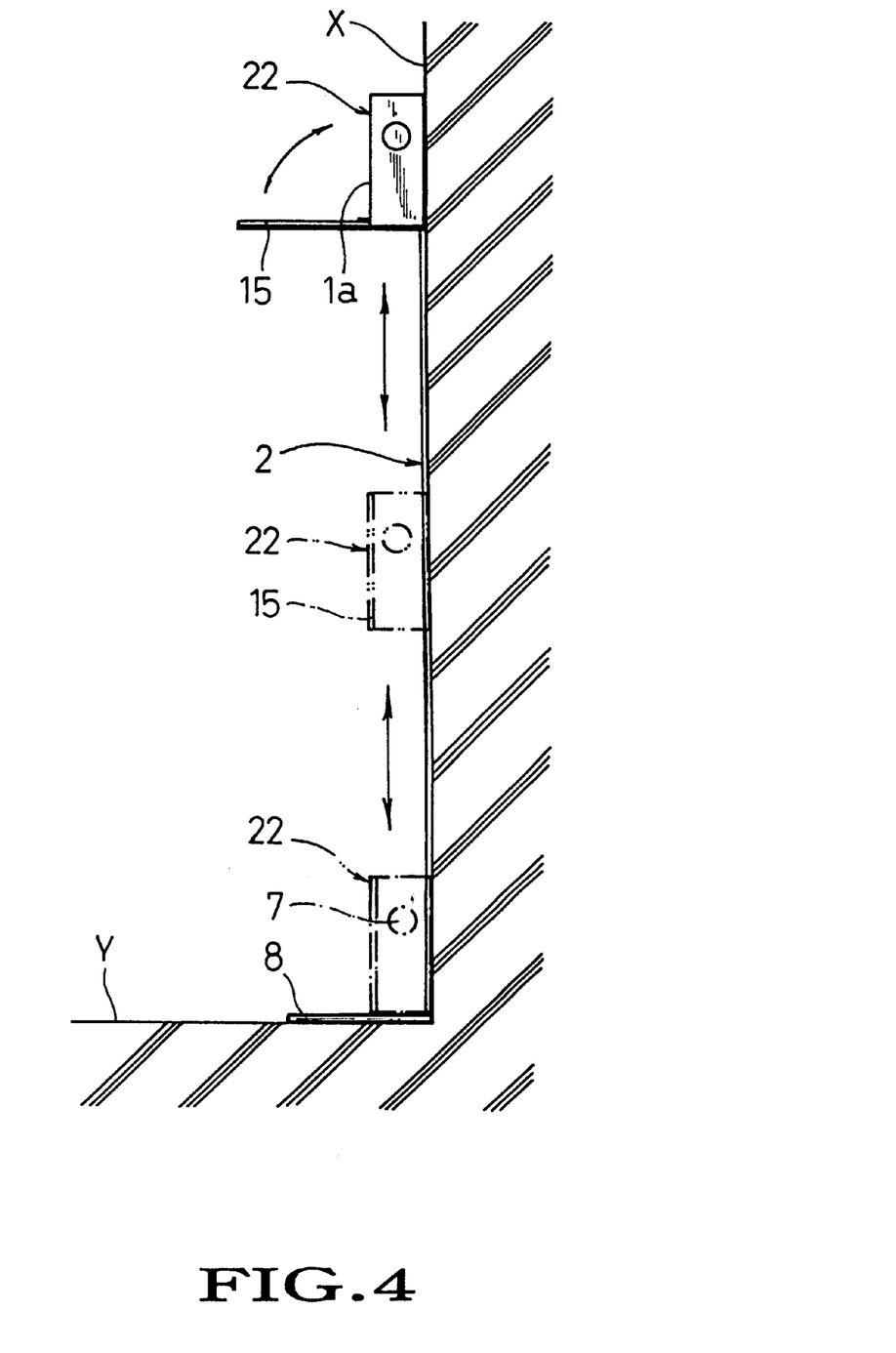
FIG. 4 is an explanatory view for extending a measuring tape showing a first embodiment of the present invention.

When it is desired to measure the height of a user Z, the user Z holds the height measuring instrument 22, opens the right-angled plate 15 as a cover. After the step 8 is pulled away from the measuring box 1 and provided at a corner between the vertical surface X and horizontal surface Y, the user Z stands on the step 7 with a barefoot, and the user Z pulls the measuring box 1 upwards. Then, the user Z pulls the desired length of the measuring tape 2 away from the measuring box 1 as shown in FIG. 4 until the right-angle plate 15 is even with a top of the user's head.

Figure 5:
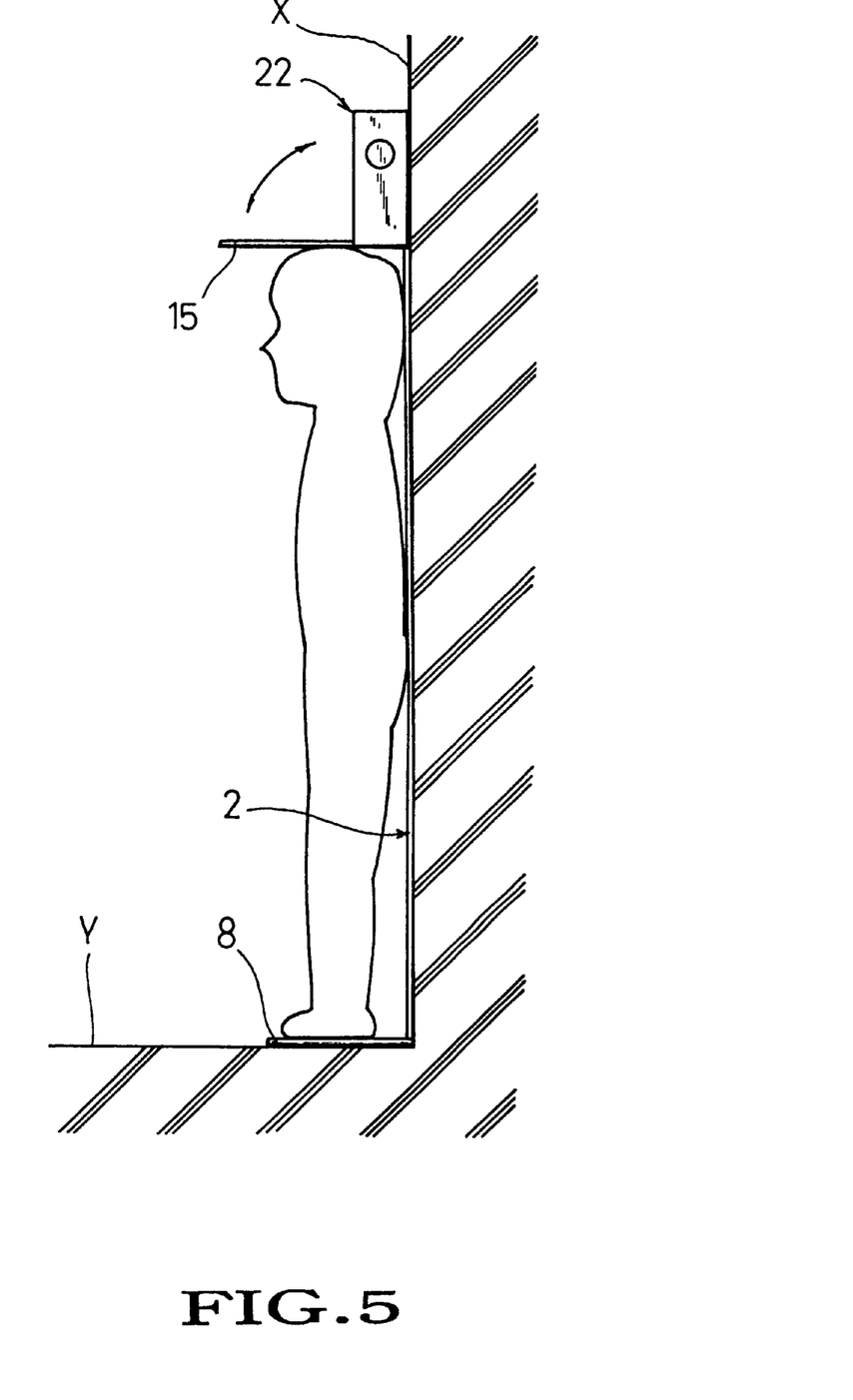
FIG. 5 is an explanatory view in use.

As shown in FIG. 5, the user Z turns the user's back on the measuring tape 2 and stands with drawing close to the vertical surface X, the measuring box 1 with the right-angled plate 15 is placed at a position above the head of the user Z. Then, the user Z can place a tension on the measuring tape 2 by turning the knobs 7, 7 such that the right-angled plate 15 of the measuring box 1 is rested upon the head of the user Z is horizontal. As a result, the measuring tape is kept the extended position thereof.

When the height of the user Z is measured, the user Z marks the punch hole 10 on the recorded space 6 of the measuring tape 2 by pushing the hole punch 4 by himself. The punch hole 10 indicates the height of the user Z. After the measuring instrument 22 is removed from the user Z, the user Z pulls the measuring tape 2 away from the measuring box 1 a little. Then, the user can mark a line 23 at the side of the punch hole 10 through the writing hole 5 on the recorded space 6 of the measuring tape 2 by writings as a pen or pencil. Thus, the line 23 and punch hole 10 on the recorded space 6 determine the height of the user Z. Also, the user can write personal data as user's own age 24 measured the height and the like adjacent the line 23 or the punch hole 10 on the recorded space 6 of the measuring tape 2.

Moreover, when it is a stored condition, the measuring tape 2 having the measured data of the height is fully wound onto the core rod 19 by turning the knobs 7,7, and it is stored within the measuring box 1 in a stored condition. At a same time period, the step 8 is retained to the bottom surface portion of the measuring box 1 through the measuring tape 2. Thus, the measuring box 1 with the measuring tape 2 therewithin and the step 8 are a compact unit for carrying and storage.

Therefore, the user can keep the measured data through the years of growth from the data of birth easily because the measuring tape 2 is marked information such as the related data, measured date by the punch hole and the like and stored in a wound condition easily and simply. In addition, the measured data is used for checking physician's records and the like in efficiency, and the measuring tape recorded the measured data thereon can be kept in commemoration for life.

Other embodiments of the present invention will now be described referring to FIGS. 6 to 8. Through the drawings of the embodiments, like components are denoted by like numerals as of the first embodiment and will not be further explained.

Figure 6:
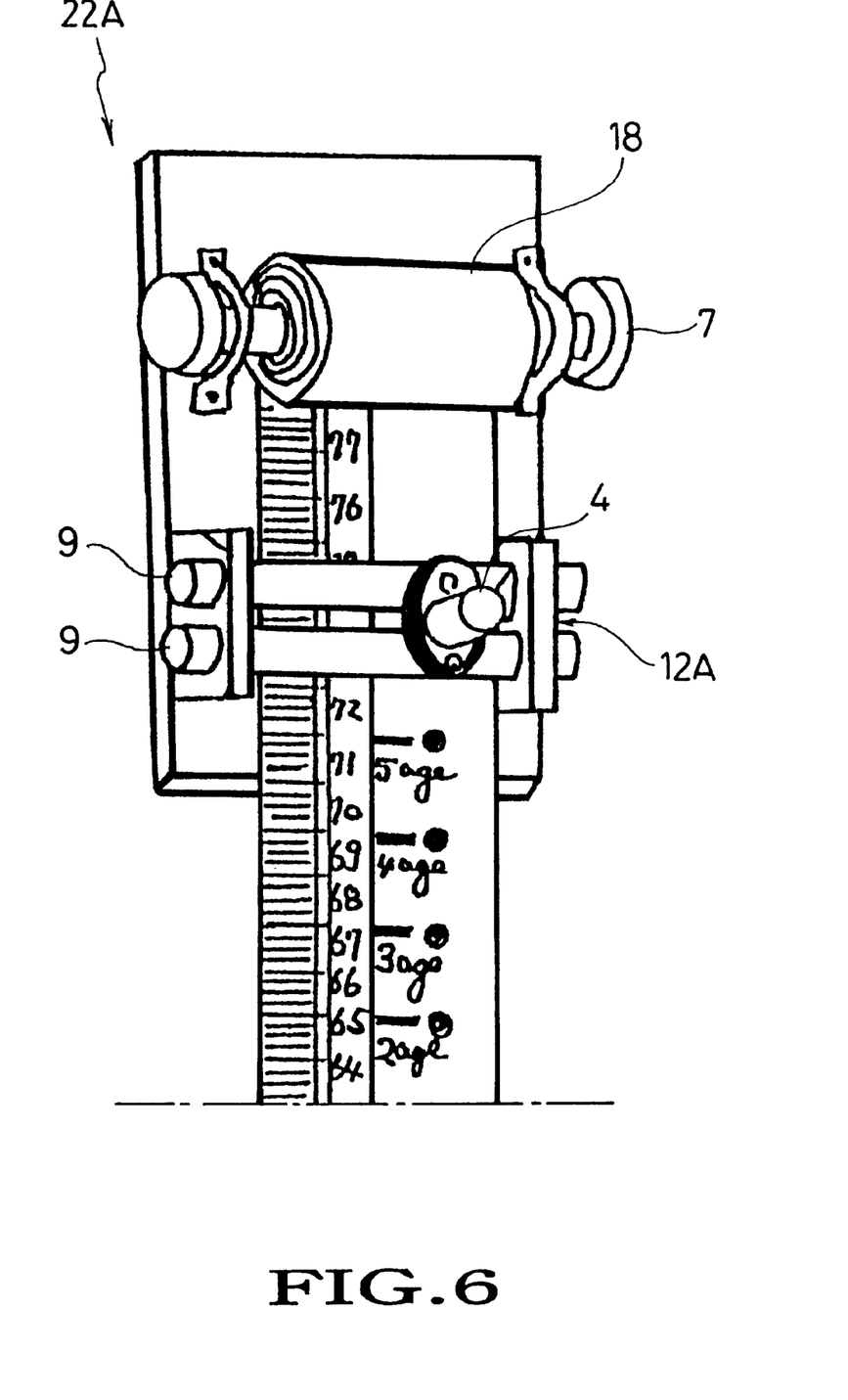
FIG. 6 is an explanatory view showing a second embodiment of the present invention.
Figure 7:
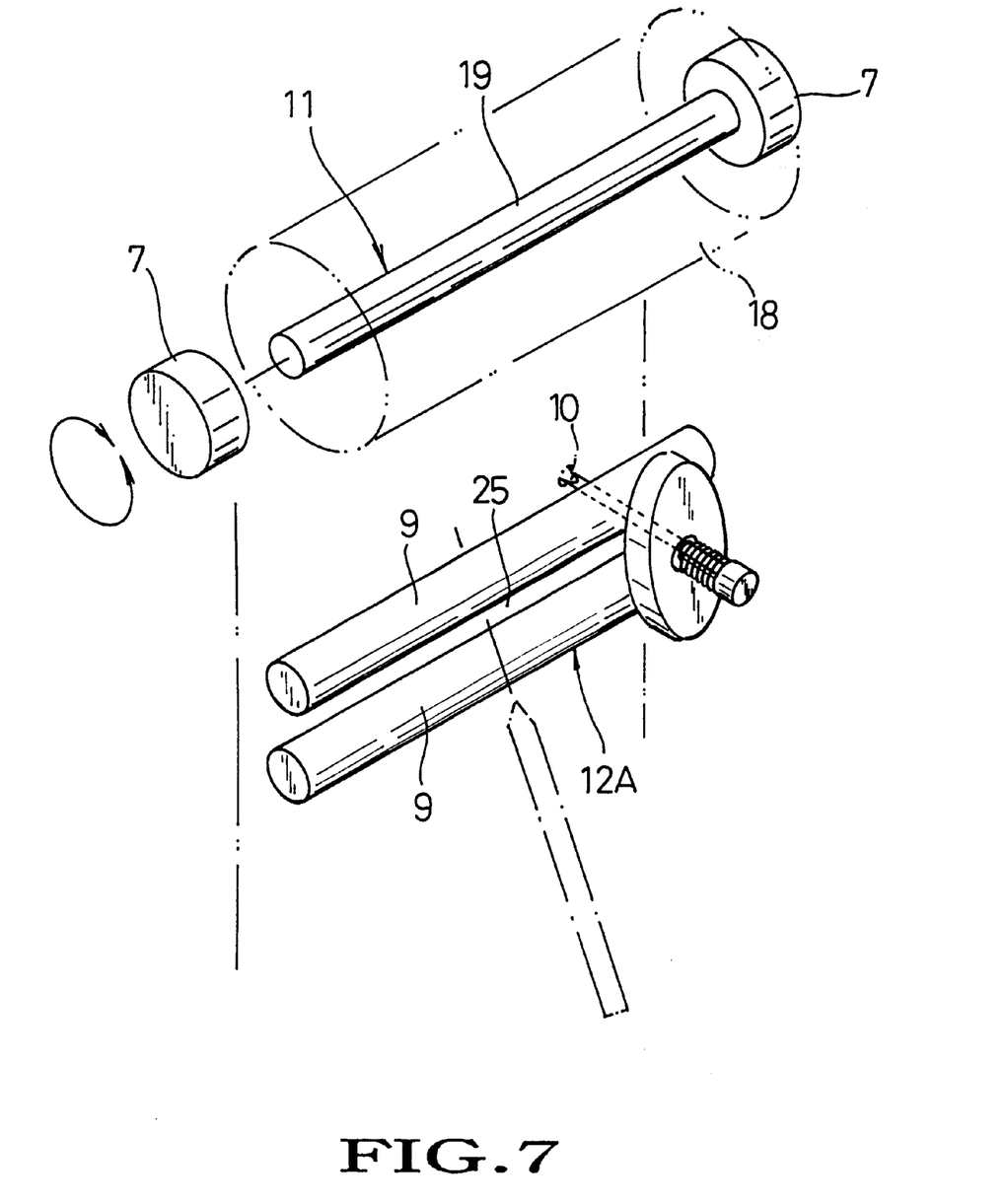
FIG. 7 is an explanatory view for a winding device of a measuring tape and a marking device showing a second embodiment of the invention.

A second embodiment of the present invention is shown in FIGS. 6 and 7. It is distinguished from the first embodiment by the fact that two measuring rods 9,9 defining a measuring member formed in a shape of a rod respectively are provided into the measuring box body 13 such that a space 25 as a writing hole is defined between the measuring rods 9,9. In addition, as shown in FIG. 7, the measuring rods 9, 9 may be supported ends thereof by plates (not number) respectively and installed into the measuring box body 13. A height measuring instrument 22A formed in this way according to the second embodiment will provide the same effects as the first embodiment.

Figure 8:
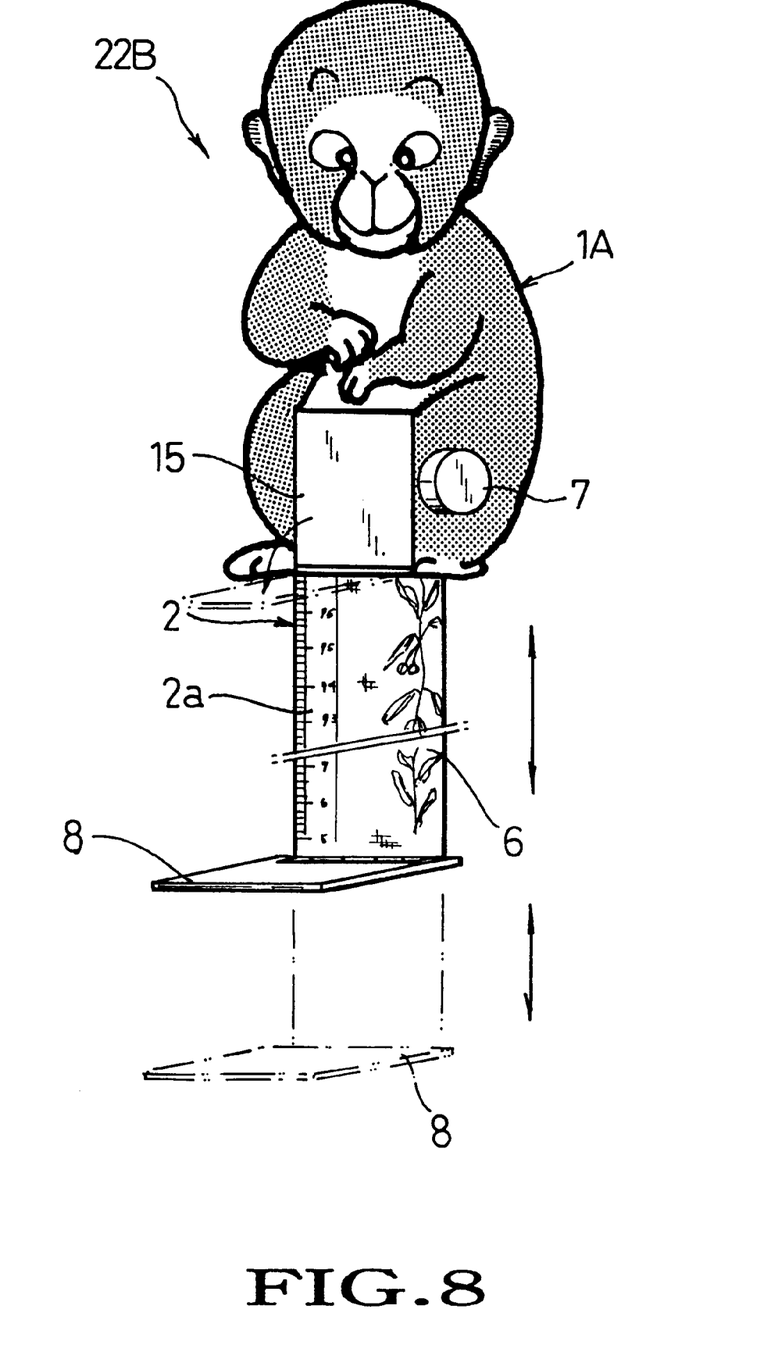
FIG. 8 is an explanatory view showing a third embodiment of the present invention.

A third embodiment of the present invention is shown in FIG. 8. It is distinguished from the first embodiment by the fact that the measuring box body 18 is formed in a shape of a monkey in this embodiment, such as a toy, character of comics, mascot, animal or the like. A height measure 22B having a measuring box 1A formed in this way according to the third embodiment will provide the same effects as the first embodiment.

In addition, the measuring tape 2 of the present invention may be printed the pictures such as plant, animal and the like and decorated.

As set forth above, the advantages of the invention are as follows:

(1) Since a height measuring instrument includes a measuring box having a right-angled plate; a measuring tape having a scale and a space to record measured data, the measuring tape wounded onto means for winding within the measuring box when in a stored mode, being extended an optional length when in an operative mode; winding means provided within the measuring box and attached to one end portion of the measuring tape so as to wind the measuring tape by handling from the outside; means for marking the measured data on the measuring tape, the marking means being included: a measuring member formed in the shape of a plate and installed into the measuring box such that the measuring member can prevent to loosen and slide the measuring tape in an operative mode by a tension on the measuring tape when in fitting of a length of the measuring tape; a through hole formed on the measuring member and allowing writing goods to pass through therein order to record a mark on the measuring tape; a hole punch having a spring provided fixedly at the measuring member such that the hole punch mark the measured data on the measuring tape; and a step attached to another end portion of the measuring tape, the height of the user is measured in a short time as done before, and the user can record the correct measured data on the measuring tape by the hole punch when in use. Moreover, the measuring tape recorded the measured data of the height can be wound onto the shaft within the measuring box easily when the instrument not in measuring use, and it is a portable simply.

Therefore, its size can be reduced simply and the cost can be reduced in efficiency.

(2) As discussed above, the measured data can be recorded continuously on the measuring tape easily and constantly, so that it can keep the measured data through the years of growth from the date of birth in efficiency, and the user can keep a history of an individual so as to check with physician's records and health care at first glance. In addition, the measuring tape recorded the measured data can be kept as memorial goods for life.

(3) As discussed above, since the measuring tape can be wound within the measuring box, the user can extend the desired length of the measuring tape during in use.

Therefore, it can adjust any changes of the height.

(4) As discussed above, the height measure can be manufactured easily because its structure is simple.

Therefore, its cost can be reduced in efficiency.

What is claimed is:

1. A height measuring instrument comprising:
   a measuring box having a right-angled plate;
   a measuring tape having a scale and a space to record measured data, the measuring tape wounded onto means for winding within the measuring box when in a stored mode, being extended an optional length when in an operative mode;
   winding means provided within said measuring box and attached to one end portion of the measuring tape so as to wind the measuring tape by handling from the outside;

means for marking the measured data on the measuring tape, the marking means being included:
  a measuring member formed in the shape of a plate and installed into the measuring box such that the measuring member prevent to loosen and slide the measuring tape in an operative mode by a tension on the measuring tape when in fitting of a length of the measuring tape;
  a through hole formed on the measuring member and allowing writing goods to pass through therein order to record a mark on the measuring tape;
  a hole punch having a spring provided fixedly at the measuring member such that the hole punch mark the measured data on the measuring tape; and
a step attached to another end portion of the measuring tape.

2. The height measuring instrument according to claim 1, wherein the measuring box is formed in a shape which is one of a toy, character of comics, mascot, and animal.

3. The height measuring instrument comprising:
  a measuring box having a right-angled plate;
  a measuring tape having a scale and a space to record the measured data and wounded upon means for winding within the measuring box when in a stored mode, being extended an optional length when in an operative mode;
  winding means provided within said measuring box and attached to one end portion of the measuring tape so as to wind the measuring tape by handling from the outside;
  means for marking measured data on said measuring tape, the marking means being included:
  a measuring member formed in the shape of two rods having an elongated space therebetween and installed within the measuring box such that the measuring member prevent to loosen and slide the measuring tape in an operative mode;
    the elongated space associated with a through hole and provided between the two rods, said elongated space allowing writing tools to pass through therein in order to record a mark the measured data on the measuring tape; and
    a hole punch having a spring provided fixedly at the measuring member such that the hole punch the measured data on the measuring tape; and
  a step attached to another end portion of the measuring tape.

4. The height measuring instrument according to claims 3, wherein the measuring box is formed in a shape which is one of a toy, character of comics, mascot, and animal.

* * * * *